(12) United States Patent
Vail

(10) Patent No.: US 6,392,460 B1
(45) Date of Patent: May 21, 2002

(54) DRIVE CIRCUIT FOR TATTOO MACHINE WHICH PROVIDES IMPROVED OPERATOR CONTROL

(76) Inventor: Walter H. Vail, 6501 N. Black Canyon Hwy., Phoenix, AZ (US) 85015

( * ) Notice: Subject to any disclaimer, the term of this patent is extended or adjusted under 35 U.S.C. 154(b) by 0 days.

(21) Appl. No.: 09/882,861

(22) Filed: Jun. 15, 2001

Related U.S. Application Data

(60) Provisional application No. 60/262,046, filed on Jan. 17, 2001.

(51) Int. Cl.$^7$ ................................................ H03K 5/12
(52) U.S. Cl. ...................................... 327/172; 327/173
(58) Field of Search ................................. 327/172, 173, 327/174, 175, 31, 37

(56) References Cited

U.S. PATENT DOCUMENTS

| | | | | |
|---|---|---|---|---|
| 4,204,173 A | * | 5/1980 | Aschwanden | ................ 331/1 A |
| 4,827,202 A | * | 5/1989 | Kurz et al. | .................. 318/608 |

* cited by examiner

*Primary Examiner*—Terry D. Cunningham
*Assistant Examiner*—An T. Luu
(74) *Attorney, Agent, or Firm*—Joseph H. Roediger

(57) ABSTRACT

A circuit for providing a pulsed signal to a driven device such as a tattoo imprinting machine wherein the pulse width and signal magnitude and frequency are controlled by the operator. A voltage controlled oscillator establishes the signal frequency, a variable impedance provides operator control of the signal magnitude and a foot-actuated switch enables the operator to control pulse width for intermittent operation. An adjustable frequency controller enables the operator to control the oscillator.

16 Claims, 4 Drawing Sheets

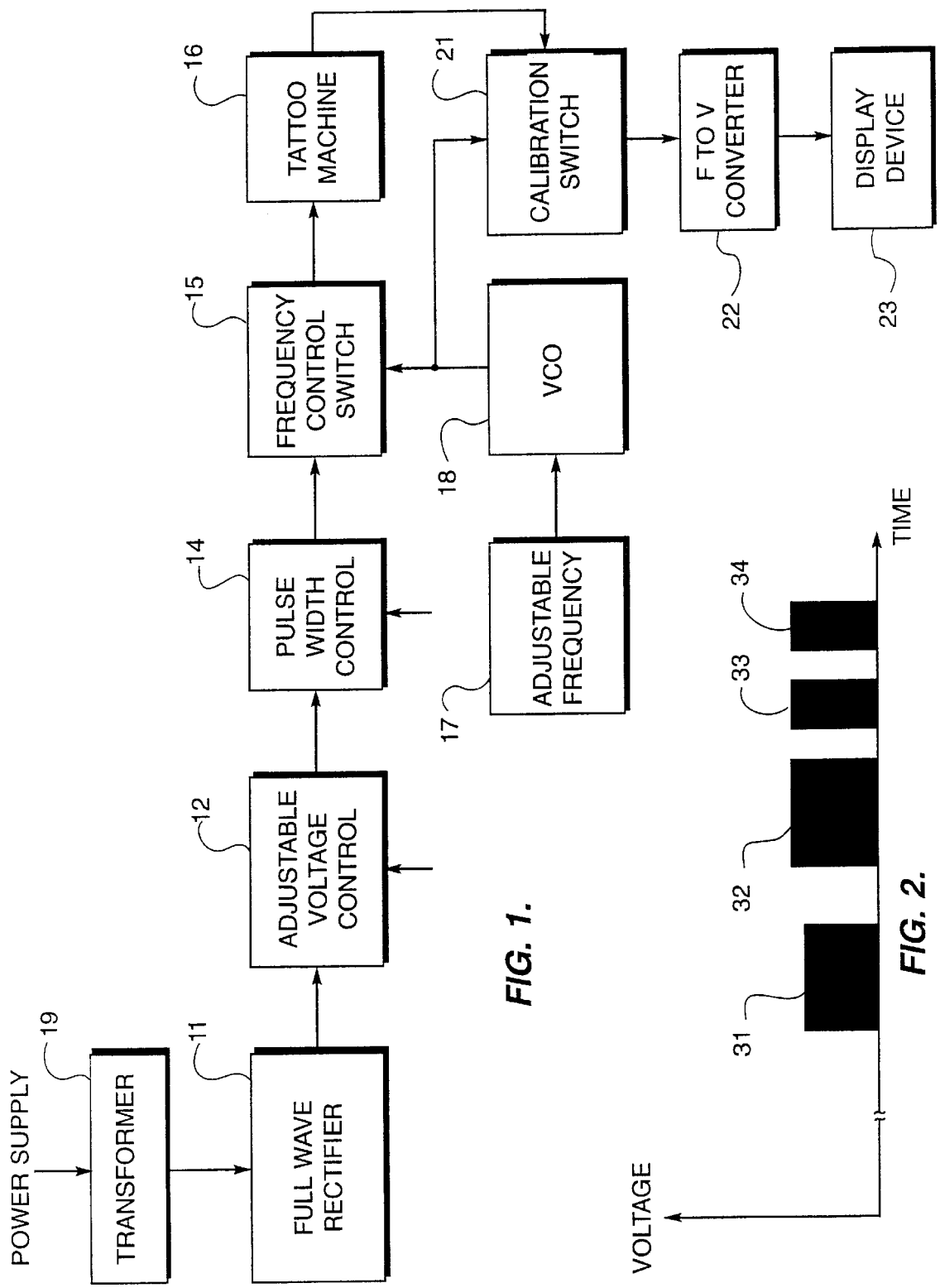

DRIVE CIRCUIT FOR TATTOO MACHINE WHICH PROVIDES IMPROVED OPERATOR CONTROL

CROSS REFERENCE TO RELATED APPLICATION

The present application is based on provisional patent application Ser. No. 60/262,046 filed Jan. 17, 2001.

BACKGROUND OF THE INVENTION

This invention relates to a circuit for providing an intermittent drive signal of variable magnitude and frequency to a driven device and in particular to the needle assembly of a tattoo machine. The subject circuit permits the operator of the driven device to manually regulate the power and frequency of the drive signal within a pulse of variable duration during utilization of the device.

The expanding numbers of people electing to carry "body art" on their anatomy has created the demand for efficient and effective equipment to imprint the desired design in an accurate manner. Typically, the process employs a tattoo machine which drives one or more components of a needle assembly in a manner which embeds dye into the user. The needle assembly may utilize a single-ended needle or a multiple-ended needle array to provide a wide variety of artistic effects and differing coloration and shading. The needle assembly includes a reservoir for the dye being used for the particular portion of the display being imprinted. At present, the moveable components of the needle assembly are driven from a dc power supply which provides a variable output in the range of 1 to 15 volts across the parallel combination of a nonlinear impedance such as a varistor and pair of series connected coils. The coils are inductively coupled to an armature which is connected to the needle assembly. The variations in the magnetic field in the coils impart the movement to the needle assembly. Variation of the power supply voltage provides the operator of the machine with the ability to vary the intensity of the motion imparted to the needle. The repetition rate of the movement of the needle is determined by the electrical characteristics of the nonlinear impedance and the coils. Thus, the frequency of the needle stroke per unit time is fixed and not under the control of the operator.

As the complexity of the images to be depicted increases, the need for increased operator control of the operation becomes more important. The effects of different coloration schemes, nonpermanent dyes and shading features have created a need for an operator to exercise control over both the intensity of the needle stroke and the frequency of the strokes during the time interval that the operator is imparting the design to the skin. Accordingly, the present invention is directed to a circuit for providing a drive signal to the driven device or needle assembly which permits the operator to establish the envelope or pulse width of a the strokes and the power and frequency of the strokes taking place within that pulse.

SUMMARY OF THE INVENTION

The present invention is directed to a circuit which permits operator control of an intermittent pulsed signal of variable magnitude and frequency to a driven device such as the needle assembly of a tatoo machine.

The circuit includes a rectifier which is coupled to the external ac supply. A series combination of an operator-variable impedance and an operator-controlled switch is coupled between the rectifier and a circuit output terminal. A circuit-controlled switch is coupled between a circuit output terminal and the rectifier with a variable oscillator providing the actuating signal to the switch. An operator-variable frequency controller is coupled to the variable oscillator to permit adjustment of the frequency of the actuating signal.

In operation, the operator-controlled switch establishes the pulse width or interval during which the operator will be making an imprint. The variable impedance enables the operator to control the voltage and the intensity of the movement of the needle. The adjustment of the frequency controller allows the operator to select the number of needle strokes within the pulse width. Thus, the operator has control of the three functions of the driven device needed to imprint complex patterns with varying visual characteristics.

Further features and advantages of the invention will become more readily apparent from the following detailed description of a preferred embodiment when taken in conjunction with the accompanying drawings.

BRIEF DESCRIPTION OF THE DRAWINGS

FIG. 1 is a block diagram of a preferred embodiment of the invention;

FIG. 2 is a diagram showing representative waveforms of the signal provided by the embodiment of FIG. 1.

DESCRIPTION OF THE PREFERRED EMBODIMENT

Figure 3A:
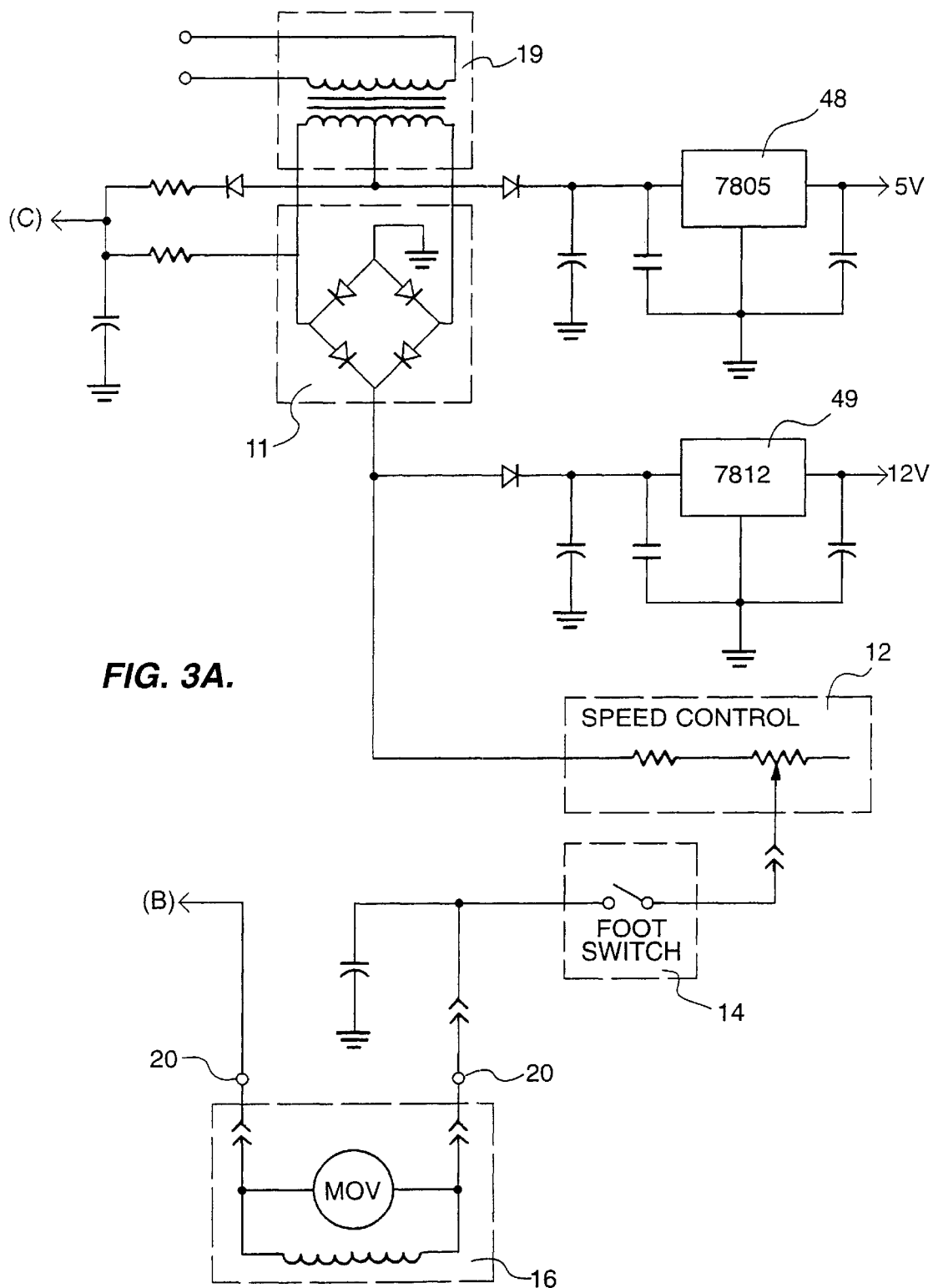
FIG. 3 is a schematic diagram of the embodiment of FIG. 1.

Referring now to the block diagram of FIG. 1, the drive circuit for a tattoo machine is shown with rectifier 11 coupled to an external ac power supply, typically 120 v 60 cycle power in the U.S. and 230 v 50 cycle in a number of foreign countries, by transformer 19. The rectifier 11 is a full wave rectifier which inverts alternate half cycles to provide a unipolar signal.

The rectifier signal is supplied to an adjustable voltage control circuit 12 which permits the operator of the tattoo machine 16 to control the magnitude of the signal thereby providing means to regulate the power supplied to the machine for driving the moveable needle to imprint the design. An improved needle assembly is described in my co-pending U.S. patent application Ser. No. 09/761,900 filed on Jan. 17, 2001 and entitled "Needle Tube Lock for Tattoo Machines," although the present invention can be used to provide a controlled drive signal for a variety of other devices including different tattoo machines.

The adjustable voltage control circuit 12 is coupled to an operator-controlled pulse width control circuit 14, which is preferably foot-operated, to allow the operator full use of both hands while imprinting the desired design. The pulse output signal defines the waveform envelope of the signal from voltage controlled oscillator 18. The oscillator 18 is controlled by adjustable frequency control circuit 17 and provides the signal to operate the frequency control switch 15. The tattoo needle is driven at the rate determined by the oscillator output signal which is operator controlled.

The output signal of oscillator 18 is also supplied via calibration switch 21 to the frequency to voltage converter 22. The output signal from converter 22 is visually displayed at display device 23 so the operator can monitor and change the frequency of the drive signal as desired. As shown in FIG. 1, the output signal from transformer 19 is supplied to calibration switch 21. The switch can be used to substitute the signal at rectifier 11 for the oscillator signal. This function enables the operator to readily check the calibration of the circuit and adjust the display device accordingly.

The circuit of the present invention enables the operator of the driven device to adjust the level of power delivered to the hand-held needle assembly, control the frequency of movement of the needle and establish the waveform of the pulse used in intermittent operation of the needle assembly. Representative waveforms are shown in FIG. 2 with pulse waveforms 31 and 32 differing in frequency and power level while pulses 33 and 34 show pulses of short duration. The differences in the waveforms and signals are shown in exaggerated form for the purpose of explanation.

Figure 3B:
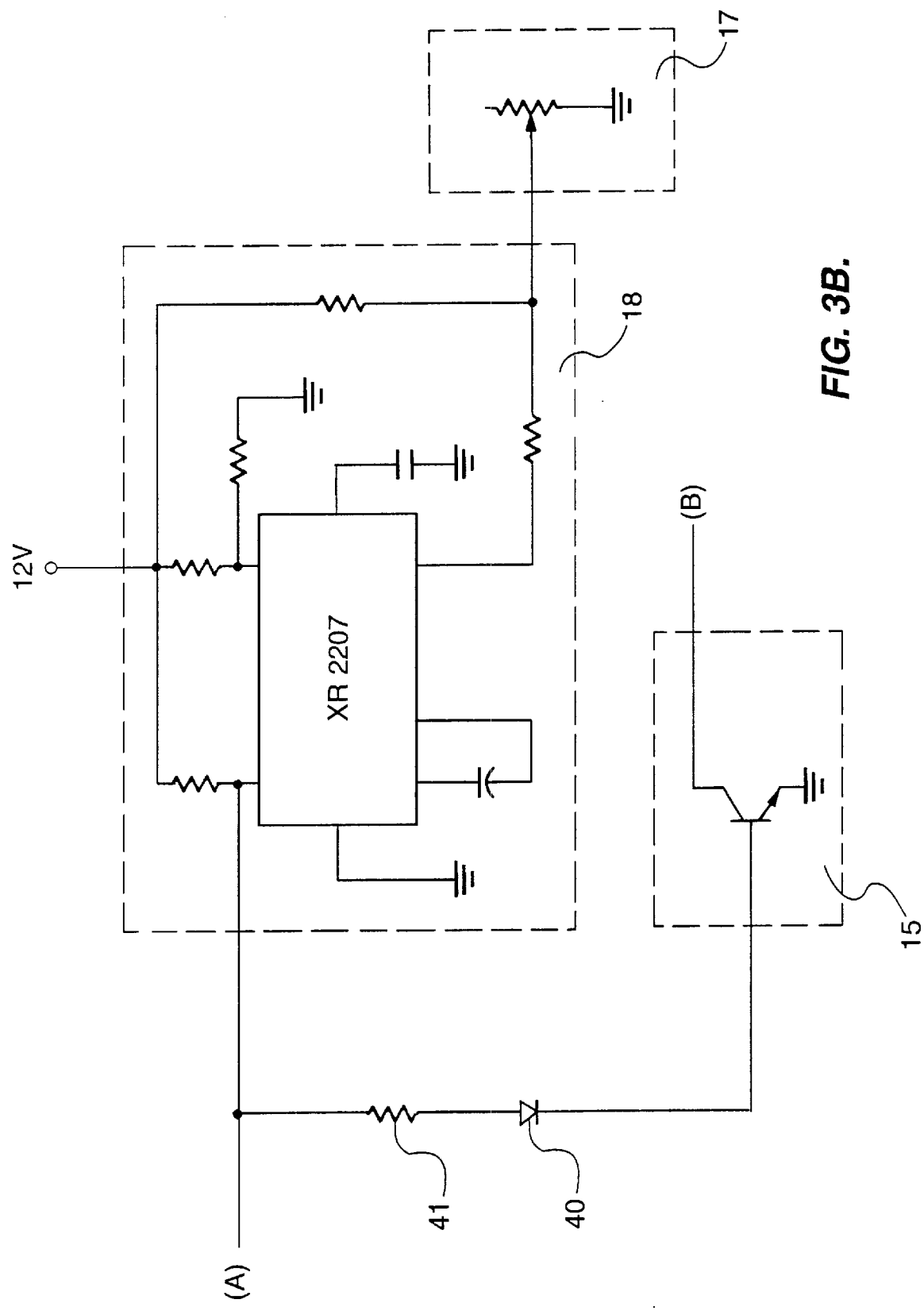
Figure 3C:
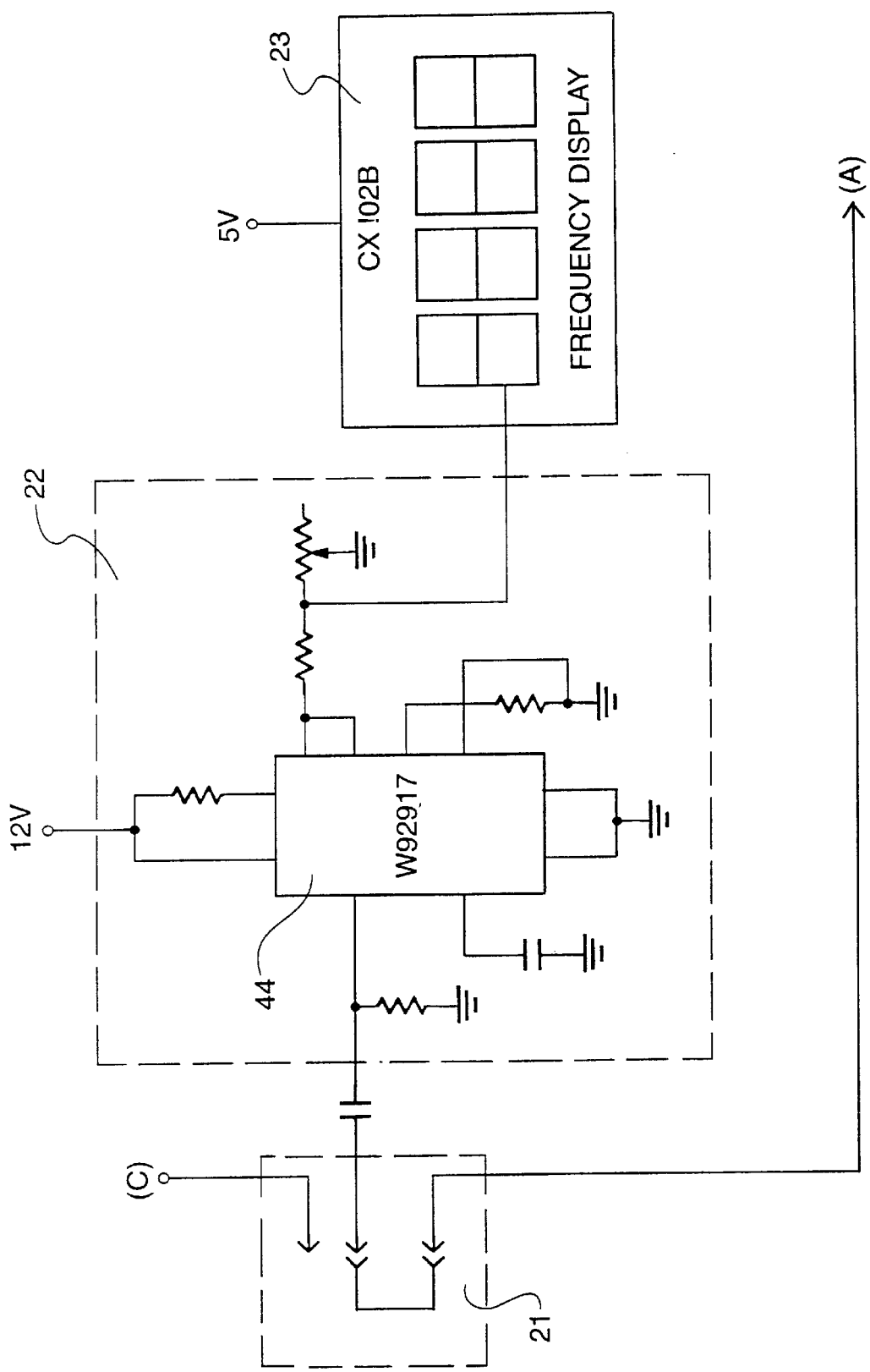

The electrical schematic diagram of the circuit of the embodiment of FIG. 1 is shown in FIG. 3. The circuit as shown includes the additional components used to provide the +5 v and +12 v levels needed for component operation. In addition, the driven device 16 is shown as the parallel combination of series inductances and a metal-oxide varistor. However, devices with other effective impedances can be coupled between output terminals 20 if desired.

Referring now to FIG. 3, the circuit input terminals receive the nominal 60 cycle 120 volt signal which is then supplied to transformer 19. The secondary of the transformer 19 provides a 12 volt ac signal to full wave rectifier 11 which supplies a positive signal to adjustable voltage control 12. Control 12 is a manually variable resistance that enables the operator to adjust the voltage appearing across the driven device 16 coupled between terminals 20. In this embodiment, the driven device is a tattoo machine wherein an inked needle is driven through a surrounding holder at varying speeds from 65 Hz to 1 Hz and at different power levels depending on the task to be performed. The operation of the tattoo machine is intermittent with the operator using a foot switch 14 to open the circuit and pause the operation.

In series with the adjustable voltage control 12, pulse width or pause control 14, and the terminals 20 is a frequency control switch 15. The switch is a transistor with a grounded emitter and a control or base electrode coupled via diode 40 and resistor 41 to voltage controlled oscillator 18. The oscillator utilizes an XR2207 microcircuit and is configured to provide a low frequency signal, typically in the 1 to 65 Hz range, with a variable impedance serving as the adjustable frequency control 17. The resistor is provided with an external knob to enable the operator to make adjustment during operation. The oscillator signal takes the transistor into and out of conduction thereby controlling the rate at which the inked needle encounters the surface upon which it is leaving an imprint. The foot switch of control 14 enables the operator to interrupt the operation without requiring a resetting of frequency or voltage level each time operation of the needle assembly is interrupted.

The input signal from the oscillator 18 is supplied via calibration switch 21 to a frequency to voltage converter circuit 22. As shown, the oscillator signal is provided to a microcircuit 44 which is a W92917 device. The output voltage from microcircuit 44 appears across the series combination of fixed resistor 46 and variable resistor 45. The tap on resistor 45 is used by the operator to calibrate the display of frequency on the LED display 23 which is identified as a CX102B device. Calibration takes placed by the movement of switch 21 to connect microcircuit 44 to the 60 Hz signal from transformer 19. If the reading at display device 23 differs, an adjustment is made by varying the resistor 45. Then, the calibration switch moved to the position shown in the drawing of FIG. 3 to resume display of the oscillator frequency.

As mentioned, the circuit shown in FIG. 3 utilizes the power supply signal as taken from the secondary of transformer 19 to derive the 5 v and 12 v supply voltages to power the circuit components. The microcircuit 48 which is a 7805 component is diode coupled to the center tap of the secondary of transformer 19 to provide a 5 v output signal to the display device. The microcircuit 49 which is a 7812 component is diode coupled to the fill wave rectifier 11 and supplies a 12 v output signal to the oscillator 18 and converter 22. All components identified by standard identifiers are manufactured by a number of companies and are commercially available.

As shown in the drawings and described herein the present invention enables the operator of the tattoo machine to readily control the number of strokes of the needle per unit of time and the power applied to drive each stroke. The pulse width control switch permits the operator to halt the operation and to resume it at his election. The description herein has been with reference to a particular embodiment of the invention and it is to be noted that modifications and variations made be made therein without departing from the scope of the invention as claimed.

What is claimed is:

1. A circuit for providing an intermittent pulsed signal of variable magnitude and frequency to a driven device, said circuit comprising:
   a) a rectifier for providing the power signal for the device;
   b) a series combination of an operator-variable impedance, an operator-controlled switch and a circuit-controlled switch coupled between the rectifier and the device, the operator-controlled switch establishing the duration of the pulse provided to the driven device, the operator-variable impedance establishing the magnitude of the pulsed signal;
   c) a variable oscillator coupled to the circuit-controlled switch for providing an actuating signal thereto, and
   d) a frequency controller coupled to the variable oscillator for varying the frequency of the actuating signal.

2. The circuit of claim 1 wherein said variable oscillator is a voltage controlled oscillator.

3. The circuit of claim 2 wherein said frequency controller is operator-controlled.

4. The circuit of claim 3 wherein said circuit-controlled switch is a semiconductor device having a control electrode coupled to the voltage-controlled oscillator.

5. The circuit of claim 4 wherein said operator-controlled switch is foot-tattoo by the operator.

6. The circuit of claim 5 further comprising a frequency to voltage converter coupled to the oscillator for generating a signal indicative of the oscillator frequency, and a display device coupled to said converter for visually displaying the oscillator frequency.

7. The circuit of claim 6 further comprising a calibration switch coupled to said converter, the actuation of said calibration switch causing the display device to visually display the power supply frequency.

8. A circuit for enabling an operator to control the pulse width, magnitude and frequency of the drive signal for a driven device, said circuit being coupled to a power supply, said circuit comprising:
   a) a series combination of manual switch, variable impedance and circuit-controlled switch coupled between the drive device and the power supply; and
   b) a variable frequency signal generator coupled to the circuit-controlled switch for controlling the operation thereof, the impedance determining the magnitude of the drive signal, the circuit-controlled switch determining the frequency of the signal and the manual switch providing control of the pulse width of the drive signal.

9. The circuit of claim 8 wherein said variable frequency signal generator comprises a variable oscillator and a frequency controller coupled thereto.

10. The circuit of claim 9 wherein said variable oscillator is a voltage controlled-oscillator coupled to the circuit-controlled switch, and said frequency controller is manually adjustable.

11. The circuit of claim 10 wherein said circuit-controlled switch is a semiconductor device having a control electrode coupled to the voltage-controlled oscillator.

12. The circuit of claim 11 further comprising a frequency to voltage converter coupled to the oscillator for generating a signal indicative of the oscillator frequency, and a display device coupled to said converter for visually displaying the oscillator frequency.

13. The circuit of claim 12 further comprising a calibration switch coupled to said converter, the actuation of said calibration switch causing the display device to visually display the power supply frequency.

14. The circuit of claim 13 wherein said power supply includes a full-wave rectifier.

15. The circuit of claim 14 wherein said manual switch is an operator foot tattoo switch.

16. A circuit for providing an intermittent pulsed signal of variable magnitude and frequency to a driven device, said circuit comprising:

a) a rectifier for providing the power signal for the circuit;

b) first and second output terminals for receiving the driven device therebetween;

c) a series combination of an operator-variable impedance and an operator-controlled switch coupled between the rectifier and the first output terminal, the operator-controlled switch establishing the duration of the pulse provided to the driven device, the operator-variable impedance establishing the magnitude of the pulsed signal;

d) a circuit-controlled switch coupled between the rectifier and the second output terminal;

e) a variable oscillator coupled to the circuit-controlled switch for providing an actuating signal thereto, and f) a frequency controller coupled to the variable oscillator for varying the frequency of the actuating signal.

* * * * *